US012636091B2

(12) United States Patent
Nadav et al.

(10) Patent No.: US 12,636,091 B2
(45) Date of Patent: May 26, 2026

(54) SMART PORT SPLITTER FOR MULTIPLE MEDICAL INSTRUMENTS

(71) Applicant: Biosense Webster (Israel) Ltd.,
Yokneam (IL)

(72) Inventors: Barak Haim Nadav, Netanya (IL);
Aviv Fux, Harish (IL); Idan Haika,
Nahariya (IL); Lior Zaritzky, Yokneam
Illit (IL); Rustam Kostenko, Karmiel
(IL)

(73) Assignee: Biosense Webster (Israel) Ltd.,
Yokneam (IL)

( * ) Notice: Subject to any disclaimer, the term of this
patent is extended or adjusted under 35
U.S.C. 154(b) by 331 days.

(21) Appl. No.: 18/537,955

(22) Filed: Dec. 13, 2023

(65) Prior Publication Data

US 2025/0195147 A1      Jun. 19, 2025

(51) Int. Cl.
    *A61B 34/20*      (2016.01)
    *A61B 6/00*       (2024.01)
(52) U.S. Cl.
    CPC ...... *A61B 34/20* (2016.02); *A61B 2034/2051*
    (2016.02); *A61B 2034/2072* (2016.02)
(58) Field of Classification Search
    CPC ................... A61B 34/30; A61B 90/37; A61B
                2017/00225; A61B 2034/2055; A61B
             34/20; A61B 2034/2051; A61B 2034/107;
                                          A61M 5/172
    See application file for complete search history.

(56) References Cited

U.S. PATENT DOCUMENTS

| | | | |
|---|---|---|---|
| 11,065,061 B2 | 7/2021 | Makower | |
| 2006/0058604 A1* | 3/2006 | Avinash | A61B 5/066 |
| | | | 600/407 |
| 2008/0200794 A1 | 8/2008 | Teichman et al. | |
| 2016/0183841 A1 | 6/2016 | Duindam et al. | |
| 2019/0090959 A1 | 3/2019 | Haider et al. | |
| 2019/0125458 A1 | 5/2019 | Shelton, IV et al. | |

(Continued)

FOREIGN PATENT DOCUMENTS

| | | |
|---|---|---|
| WO | 2019133136 A1 | 7/2019 |
| WO | 2023002393 A1 | 1/2023 |

OTHER PUBLICATIONS

Extended European Search Report, received for European Application No. 24219263.1, mailed on May 12, 2025, 9 pages.

*Primary Examiner* — Jon Eric C Morales

(57) ABSTRACT

An apparatus includes input channels, output channels, a control channel, and switching circuitry. The input channels receive position signals from multiple medical instruments located in an organ of a patient. The output channels forward one or more of the position signals to a position tracking system. The control channel receives control signals from the position tracking system. The switching circuitry forwards at least some of the position signals to the output channels in accordance with a first switching scheme, receives from the position tracking system, over the control channel, in response to the forwarded position signals, a control signal indicative of a given medical instrument that was identified as being located within a working volume of the position tracking system, and switches to a second switching scheme, in which all the position signals of the given medical instrument are forwarded to at least some of the output channels.

16 Claims, 6 Drawing Sheets

(56) References Cited

U.S. PATENT DOCUMENTS

| | | |
|---|---|---|
| 2019/0201142 A1 | 7/2019 | Shelton, IV et al. |
| 2020/0305924 A1 | 10/2020 | Carroll |
| 2022/0313373 A1 | 10/2022 | Morgan et al. |
| 2023/0022604 A1 | 1/2023 | Shelton, IV |

* cited by examiner

CONTROL CHANNEL

→ initial phase

OUTPUT CHANNELS initial phase ┈┈┈ 308

306

X ◄──── X1

Y ◄──── Y1

Z ◄──── Z1

INPUT CHANNELS

X1

Y1    from first
      medical
Z1    instrument track
phase -
select first track select    304 initial phase

X2

Y2    from second
      medical
Z2    instrument track select    304 track
phase -
select
second initial phase

X3

Y3    from third
      medical
Z3    instrument track select    304 track
phase -
select
third

SMART PORT SPLITTER FOR MULTIPLE MEDICAL INSTRUMENTS

FIELD OF THE DISCLOSURE

The present disclosure relates generally to medical probes, and particularly to in-vivo tracking of medical probes.

BACKGROUND OF THE DISCLOSURE

Techniques to guide an invasive probe inside a cavity of an organ to target tissue have been previously proposed in the patent literature. For example, U.S. Patent Application Publication 2019/0090959 describes improvements related to computer aided surgery (CAS) utilizing an on-board tool tracking (OTT) system. Some of the improvements relate to methods of providing feedback during a procedure to improve either the efficiency or quality, or both, for a procedure including the rate of and type of data processed depending upon a CAS mode. In an example, to provide navigation assistance during an OTT CAS procedure, an OTT device monitors the position of the associated surgical tool within the surgical field. The OTT CAS system may use none, or one or more reference frames, including one or more position sensors or one or more fiducial markers depending upon the requirements of the OTT CAS procedure being undertaken.

As another example, U.S. Patent Application Publication 2016/0183841 describes a method of guiding an interventional instrument within a patient anatomy that comprises processing a target location within the patient anatomy and receiving a position for a tip portion of an interventional instrument at a first location within the patient anatomy. The method also comprises determining a three-dimensional distance between the first location and the target location and displaying a symbol representing the target location and a symbol representing the tip portion of the interventional instrument. In an example, a rotational orientation of a feature of the distal tip portion may also be displayed by the navigation aid image with a rotation assistance symbol. For example, if a biopsy instrument has a side opening, the side with the opening may be indicated on the navigation aid image with the rotation assistance symbol.

U.S. Pat. No. 11,065,061 describes devices, systems and methods for performing image guided interventional and surgical procedures, including various procedures to treat sinusitis and other disorders of the paranasal sinuses, ears, nose or throat. In some applications, a preoperative tomographic scan (e.g., a CT scan) may be obtained and the image guidance system may be programmed to display the tomographic images on a video monitor along with a real time indication (e.g., cross hairs, an illuminated dot, etc.) of the location of the working device relative to the anatomical structures shown on the tomographic image.

DETAILED DESCRIPTION OF EXAMPLES

Overview

Figure 1:
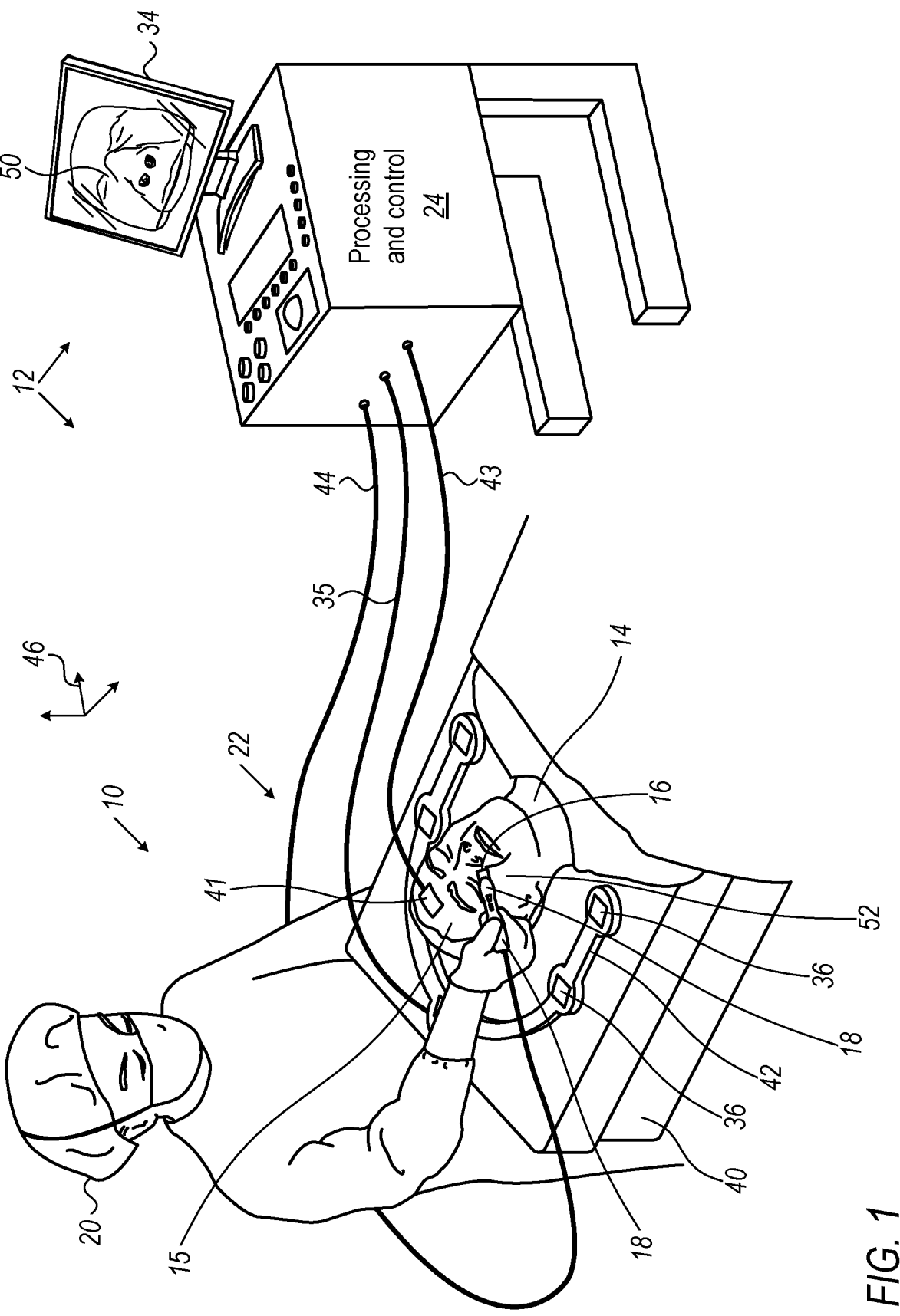
FIG. 1 is a schematic, pictorial illustration of an ear-nose-throat (ENT) system, in accordance with an example of the present disclosure.

A distal end section of a probe, such as an ear-nose-throat (ENT) probe used with a guiding system, can be tracked to be visually used as a cursor (i.e., pointer) of a location in a 3D view (e.g., medical image) of a cavity of a patient. For example, an ENT suction tool, or a shaver, can be used in such a way with the TruDi™ ENT tracking system (made by Acclarent, Irvine, California). The medical image can be generated, for example, from a Computerized Tomography (CT) or a Magnetic Resonance Imaging (MRI) image.

The distal end section of the probe (e.g., an ENT suction device) can be tracked using a magnetic sensor (e.g., a coil) attached to the distal end, with the tracked position projected onto a location on the medical image. We will refer here-inbelow to the tools that can be used with the ENT tracking system as medical instruments; each such medical instrument is assumed to generate an electric signal responsively to a location-dependent magnetic field, and, thus, allow the tracking of the position of the medical instrument within the cavity of the patient.

In practice, the tracking system has a limited number of input channels for receiving signals from magnetic of medical instruments. When multiple medical sensors instruments are in use during a medical procedure, the tracking system may be unable to track all medical instruments at the same time. However, at any given time only a subset of the medical instruments may be within a working volume in which the medical procedure is carried on, and, often, the tracking system may be required to track only a single instrument or a small number of instruments at a time.

Examples of the present disclosure that are described hereinafter provide methods and systems that allow automatic detection (during an Initial Phase) and tracking (during a subsequent Tracking Phase) of medical instruments that are in the working volume. The disclosed techniques allow the overall number of position sensors of the medical instruments to exceed the number of input channels of the tracking system, by detecting which medical instruments are within the working volume and prioritizing the position signals of these instruments.

In an example, the tracking system comprises a Smart Port Splitter (SPS) that selects a subset of the position indication signals input over input channels from the medical instruments, and forwards the subset, over output channels, to a Position Tracking System (PTS).

In some examples, in the Initial Phase, the sensors in the medical instruments are triple-axis sensors, each producing an X position signal, a Y position signal and a Z position signal. the SPS forwards the X position signals of three medical instruments to the PTS (e.g., to the X, Y and Z output position indication signals). Based on the three X position signals, the PTS detects which, if any, of the three medical instruments is in the working volume. Once such an instrument is detected, the tracking system enters the Tracking Phase, wherein the X, Y and Z position signals of the detected instruments are forwarded to the PTS, and then projected on the medical image.

In another example, the SPS, at the Initial Phase, continually scans all sensors of all instruments in time division and forwards the position indication signals of each instrument to the PTS. The PTS checks if any instrument is in the working volume. If such an instrument is detected, the tracking system enters the Tracking Phase, stops the Scan and tracks the detected medical instrument.

In a variant of the example described herein above, the SPS comprises peak detectors and comparators, and the Scan includes only instruments for which the position indication signal strength is above a preset threshold.

System Description

FIG. 1 is a schematic, pictorial illustration of an ear-nose-throat (ENT) system 10, in accordance with an example of the present disclosure. System 10 is used to register a position-tracking system 12 with an image (for example, a computerized tomography (CT) image), of an organ 15 (e.g., a head) of a patient 14.

Position-tracking system 12 may comprise, for example, a magnetic tracking system. The Carto® system, produced by Biosense Webster, of Irvine, Calif., uses a tracking system similar to that described herein to track the location and orientation of the distal tips of a probes inserted into or brought into the vicinity of a patient.

Position-tracking system 12 is to used track positions and orientations of one or more instruments, such as catheters or guidewires, that are inserted into patient 14 during a medical procedure performed on the patient.

As is described below, position-tracking system 12 is also able to track the position and orientation of a registration probe 16 that is external to the patient. Probe 16 is fixedly connected to a handle 18 that may be held by a medical practitioner 20, typically a physician, during use of system 10. The combination of probe 16 and handle 18 form a rigid probe assembly 22 that facilitates the positioning by physician 20 of the probe to a desired location.

For clarity and simplicity in the following description, the medical procedure referred to above is assumed to comprise an invasive procedure on a nasal sinus of patient 14, so that ENT system 10 and position-tracking system 12 are assumed to be configured to operate in and around the region of the nasal sinus. However, systems 10 and 12 may alternatively be configured to operate in and around other regions of a patient, such as the thorax, kidneys or abdomen, or other regions. Furthermore, the principles of the present disclosure may be applied in conjunction with other types of tracking systems (not necessarily magnetic), as well as other sorts of 3D imaging modalities, such as Magnetic Resonance Imaging (MRI).

Tracking system 12 is operated by processing and control 24, comprising a position tracking system, a smart port splitter (to be described below) and a processor that is configured to receive a 3D map (e.g., CT map) of a region of interest within organ 15 of patient 14, and render an image comprising cross-section of the organ and an indication of the location of the medical instrument in the organ. The image is displayed on a monitor 34.

In order to track the instruments referred to above within patient 14, processing and control 24 operates, via a cable 35, a plurality of magnetic field generators 36, such as coils. In one example, typically applicable if patient 14 is anesthetized and head 15 is immobile, generators 36, as illustrated in FIG. 1, are fixed to a frame 42 placed on the bed, beside the patient's head. In shown), applicable if an alternative example (not patient 14 is not anesthetized, generators 36 are fixed with respect to each other and to a frame attached to head 15 or to a chair in a physician's office. A three-axis reference coil 41 is fixed to head 15, and connected to processing and control 24 by a cable 43.

Generators 36 radiate alternating magnetic fields into and around head 15 of patient 14, and these fields generate signals in magnetic detectors in the instruments and in probe 16. The signals are conveyed back to processing and control 24 via a cable 44 connecting probe 16 to processing and control 24, which analyzes the signals to derive location and orientation coordinates of the instruments and probe 16 with respect to generators 36. Magnetic field generators 36 thus define a coordinate frame of reference 46 of magnetic tracking system 12.

At any given time, some (or all) the medical instruments that are not used may be remote from the magnetic field generated by Magnetic field generators 36, while other medical instruments, e.g., instruments that are inserted into organ 15, may be near the magnetic field. For medical instrument tracking purposes, we define a working volume that includes organ 15; all instruments within the working volume are subject to the magnetic field and generate position indication signals; instruments outside the working volume may or may not generate position indication signals (or, sometimes, generate weak indication signals that are not useful for tracking purposes).

Reference Coil 41, which is in the magnetic field but is placed on top rather than in organ 15 is used for reference to indicate movements of the organ; the position of Reference Coil 41 is typically not displayed on monitor 34 and, therefore, in the description hereinbelow the term medical instruments will not include Reference Coil 41.

Selecting Instruments for Display

In some examples, a plurality of medical instruments may be used in one medical procedure, albeit not all at the same time. Each medical instrument may output a plurality of position indication signals, e.g., three signals for 3-D position coordinates. In an example, the total number of the position indication signals exceeds the capacity of the processing and control circuit. In some examples, during the medical procedure, physician 20 may insert and remove instruments from the working volume (e.g., head 15). The total number of the position indication signals output by instruments that are in the working volume fits the capacity of the processing and control circuit, which is then able to track and display all instruments in the working volume. In an example, at any given time, no more than one medical instrument may be within the working volume.

Figure 2:
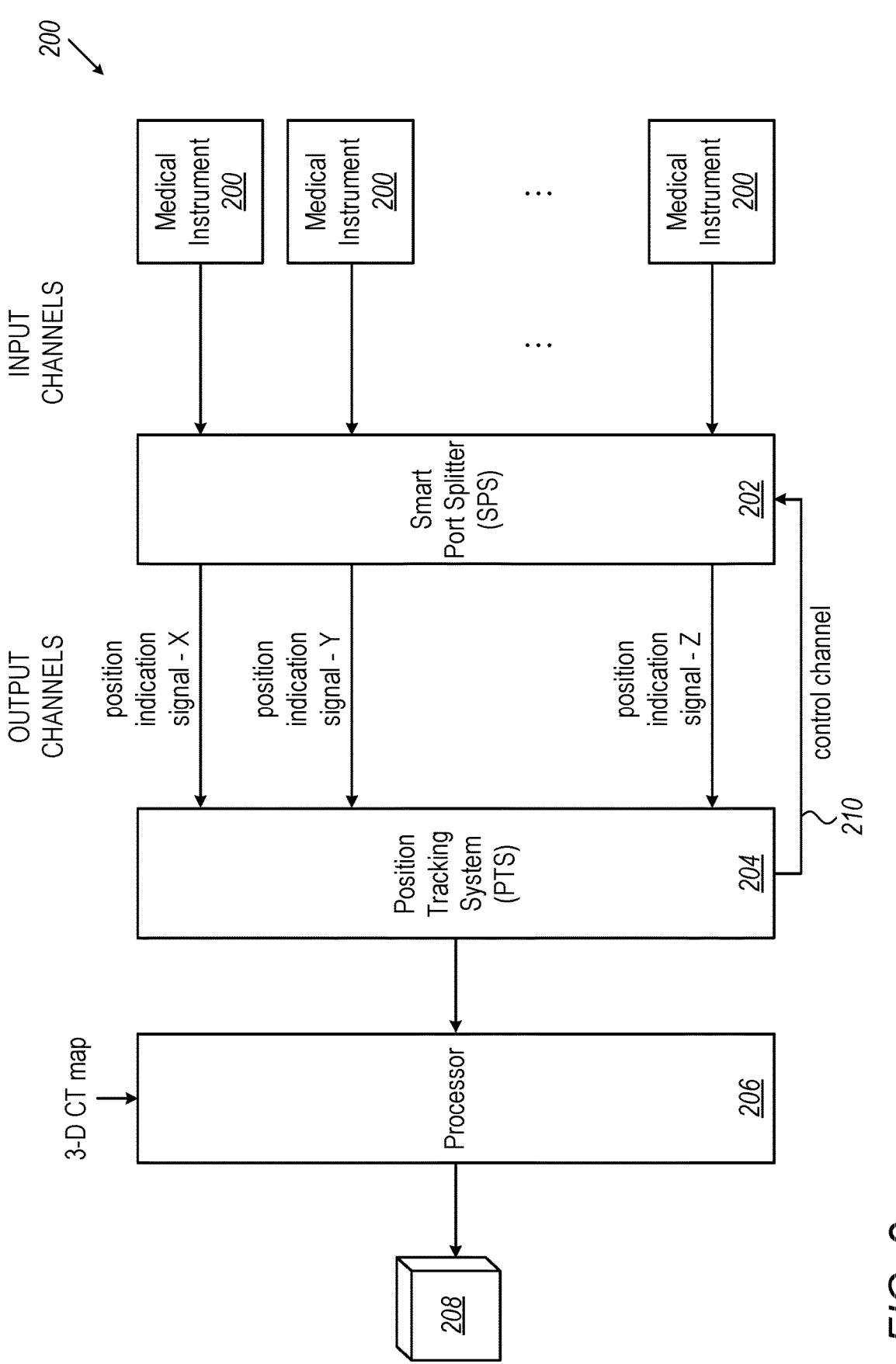
FIG. 2 is a block diagram that schematically illustrates a tracking and display system, in accordance with an example of the present disclosure.

FIG. 2 is a block diagram that schematically Fig. illustrates a Tracking and Display System 200, in accordance with an example of the present disclosure.

Tracking and Display System 200 comprises a plurality of medical instruments 202, a Smart Port Splitter (SPS) 202, a Position Tracking System (PTS) 204, a Processor 206 and a Display 208.

Some, or all, of Medical Instruments 200 may be inserted in an organ of the patient. The instruments include one or more position sensing coils that generate an electric signal indicative of the medical instrument's position in response to a magnetic field (generated, for example, by field generators 36, FIG. 1). Some medical instruments comprise position sensing coils that generate signals indicative to the 3-D position of the medical instrument; other medical instruments may generate one-or two-dimension position signals, and yet other medical instruments generate signals indicative to the tilt and rotate of the medical instrument (in addition or in lieu of the position indication signals).

Examples of suitable medical instruments include Suctions, Probes, Curettes, Endoscopes, Drills and others.

SPS 202 is configured to receive position indication signals from medical instruments over a plurality of input channels, and to forward a subset of the position indication signals to a plurality of output channels that are input to the PTS. In the example illustrated in FIG. 2, the PTS is configured to track a single medical instrument and, hence, the output channels comprise an X position signal, a Y position signal, and a Z position signal. In another example (that will be described with reference to FIG. 4), the SPS is configured to output, and the PTS is configured to track two instruments (but the PTS sends coordinates of a single instrument only to processor 206).

The input channels subset is selected according to a switching indication that is input to the SPS from the PTS, over a Control Channel 210.

PTS 204 is configured to calculate the positions of the medical instruments responsively to position indication signals, and to send the calculated positions to processor 206. In an example, the calculated positions include the positions of a medical instrument that is in the working volume. In another example, the calculated positions include the positions of two medical instruments. In both examples, the PTS sends the coordinates of one medical instrument only to the processor.

Processor 206 receives a 3-D position indication of the medical instrument from the PTS and a 3-D map of the organ (generated, for example, by a Computerized Tomography (CT) device), and displays a cross-section of the organ with an indication of the medical instrument overlaid on the cross-section.

In examples, Tracking and Display System 200 may be in one of two distinct operating phases—a first phase, in which no medical instrument is tracked, and a second phase, in which a medical instrument in the working volume is tracked. According to the example illustrated in FIG. 2, the PTS determines the operating phase responsively to the position indications. While in the first phase, the SPS forwards the input channels to output channel according to a first switching scheme and, while in the second phase, according to a second switching scheme.

We will sometimes refer to the first and second operating phases, respectively, as the Initial Phase and the Tracking Phase; similarly, we will sometimes refer to the first and second switching schemes as the initial switching scheme and the tracking switching scheme).

In examples, processor 206 may comprise one or more general-purpose processors, which are programmed in software to carry out the functions described herein. The software may be downloaded to the processor in electronic form, over a network or from a host, for example, or it may, alternatively or additionally, be provided and/or stored on non-transitory tangible media, such as magnetic, optical, or electronic memory.

One-Dimension Detection

In a One-Dimension-Detection example, the SPS, while in the Initial Phase, outputs position indication signals pertaining to a single dimension in the plurality of medical instruments. For example, if there are three medical instruments A, B and C, the SPS may, while in the Initial Phase, forward the X position signal of medical instrument A to the X position output of the SPS, forward the X position signal of instrument B to the Y position output of the SPS, and, forward the X position signal of instrument C to the Z position output of the SPS. The PTS will detect an instrument in the working volume (if any) by calculating the position of a combined instrument, with X, Y and Z dimensions equal to the X dimension of instruments A, B and C, respectively. If the position, in any of the X, Y and Z dimension, is in the working volume, the PTS will determine (and signal to the SPS) that the Tracking Phase should start and detect the instrument according to the dimension; the SPS will now forward the input channels to the output channels according to a second switching scheme, in which all the input channels pertaining to the detected instrument are forwarded (e.g., the PTS forwards the X, Y and Z position signals of the detected instrument to the X, Y and Z output channels); the PTS will now track the position of the detected instrument. (It should be noted that the using of the X dimension only, as described in the example above, is arbitrary; any other dimensions may be used in alternative examples, including a selection of arbitrary dimensions from each input instrument (e.g., Z of the first instrument, Z of the second instrument, and Y of the third instrument).)

Time-Division-Multiplex Detection

In a Time-Division-Multiplex Detection example, the SPS, while in the Initial Phase, forwards input channels to the output channel according to a first switching scheme that comprises Time-Division-Multiplex. For example, in a first timeslot, the X, Y and Z position indication signals of a first medical instrument are forwarded, respectively, to the X, Y and Z output channels; in a second timeslot, the position indication signals of a second medical instrument are forwarded to the output channels, and so on (in a cyclic manner).

Thus, PTS 204 sequentially calculates the positions of the medical instruments. If any of the instruments is in the working volume, the PTS will determine (and signal to the SPS) that the Tracking Phase should start; the SPS will then forward the position signals of the medical instrument in the working volume to the output channels, and the PTS will continually track the position of the instrument.

In another Time-Division-Multiplex Detection example, SPS 202 further comprises a threshold pre-selector that compares the strength (e.g., voltage) of the position indication signals to a preset threshold. The time-division multiplexing will forward only instruments with position indication signals above the preset threshold and, thus, instruments that are remote from the working volume (e.g., in an instrument tray, ready to be used) will not be multiplexed. This decreases the number of time slots, allowing faster detection of an instrument in the working volume.

In some examples, the SPS is configured to output the coordinates of two instruments at the same time: a first coordinates set of a medical instrument to be tracked, and a second set that is time-division-multiplexed between some or all of the other medical instruments. One such example will be described below, with reference to FIG. 6.

The configuration of Tracking and Display System 200 illustrated in FIG. 2 and described herein above is cited by way of example. Other configurations may be used in alternative examples. In an example, some of the medical instruments are always input to the PTS, bypassing the SPS. In another example, processor 206 functionality includes Position Tracking, and PTS 204 is not implemented.

Figure 3:
FIG. 3 is a block diagram that schematically illustrates a smart port splitter (SPS) that is configured for one-dimension detection, in accordance with an example of the present disclosure.

FIG. 3 is a block diagram that schematically illustrates a smart port splitter (SPS) 300 that is configured for One-Dimension Detection, in accordance with an example of the present disclosure. According to the example illustrated in FIG. 3, SPS 300 comprises nine input channels that are connected to the X, Y and Z position signals of three medical instruments, and three output channels, comprising X, Y and Z position signals.

The SPS receives a phase indication (e.g., from PTS 204, FIG. 2) over the control channel, comprising an Initial Phase indication and three Track-Phase indications. During the Initial Phase the Initial Phase Indication is set, whereas during the Tracking Phase one of the three Track-Phase indications (Track-First, Track-Second or Track Third) is on, according to the instrument to be tracked.

The X, Y and Z position signals from the three medical instruments are connected to three switch-assemblies 304. Each switch assembly comprises four on-off switches—three switches 306 that are on (connected) if the instrument is tracked during the Tracking Phase (responsively to a track-select input), and a switch 308 that is on during the Initial Phase.

In examples, switch 306 and 308 may comprise metal-oxide-silicon (MOS) transistors; in an example, a combination of an N-type MOS (NMOS) and P-type MOS (PMOS) transistors are used. In some examples, the position indication signals comprise pairs of wires (e.g., when the position indication signals are complementary differential signals) and, hence, each of switches 306, 308 comprises two switches.

During the Initial Phase, the input channels are forwarded to the output channels according to the Initial Scheme—the X position signal of the first medical instrument is forwarded to the X position output signal, the X position signal of the second medical instrument is forwarded to the Y position output signal, and the X position signal of the third medical instrument is forwarded to the Z position output signal. The PTS will, therefore, receive the 3-D coordinates of a combined virtual instrument, with its X Y and Z positions equal respectively, to the X position signal of the first, second and third medical instruments. By determining if the position in any of the dimensions is within the working volume, the PTS detects a medical instrument to be tracked, and activates a Track-Phase-Select signal accordingly.

The configuration of One-Dimension Detection SPS 300 illustrated in FIG. 3 and described above is cited by way of example. Other configurations may be used in alternative examples. In an example, other dimensions of the input instruments may be forwarded in the Initial Phase, e.g., the Y dimension, or a mix of different dimensions.

Figure 4:
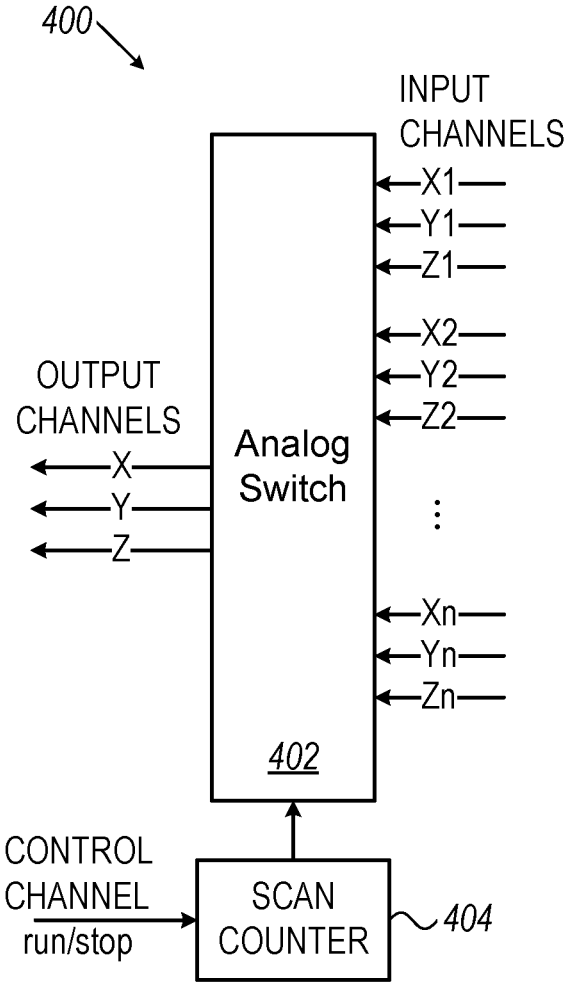
FIG. 4 is a block diagram that schematically illustrates the structure of a Time-Division-Multiplex detection SPS, in accordance with an example of the present disclosure.

FIG. 4 is a block diagram that schematically illustrates the structure of a Time-Division-Multiplex detection SPS 400, in accordance with an example of the present disclosure. The SPS comprises an Analog Switch 402 and a Scan Counter 404. The SPS receives X, Y and Z position indication signals from n instruments over the Input Channels, and outputs selected X, Y and Z position indication signals over the output channels. According to the example illustrated in FIG. 3, the Control channel includes a single run/stop indication, that is input to a Scan Counter 404 over the Control Channel.

During the Initial Phase, the PTS sends a Run indication to the SPS. Responsively, the Scan Counter counts continuously (e.g., from zero to the number of medical instruments minus 1, wrapping back to zero). The count is input to Analog Switch 402, which forwards the position signals of the corresponding medical instruments to the output channels.

To detect a medical instrument to be tracked, the PTS checks for every input medical instrument, if the instrument is in the working volume. When a medical instrument to be tracked is detected, the Track Phase is entered—the PTS stops the Run output and the Scan Counter stops counting. The Analog Switch continues to forward the X, Y and Z position signals of the detected medical instrument to the PTS, for tracking.

The configuration of Time-Division-Multiplex SPS 400 illustrated in FIG. 4 and described above is cited by way of example. Other configurations may be used in alternative examples. For example, the PTS may output the scan count to the SPS, and the Scan Counter is not used.

Figures 5, 6:
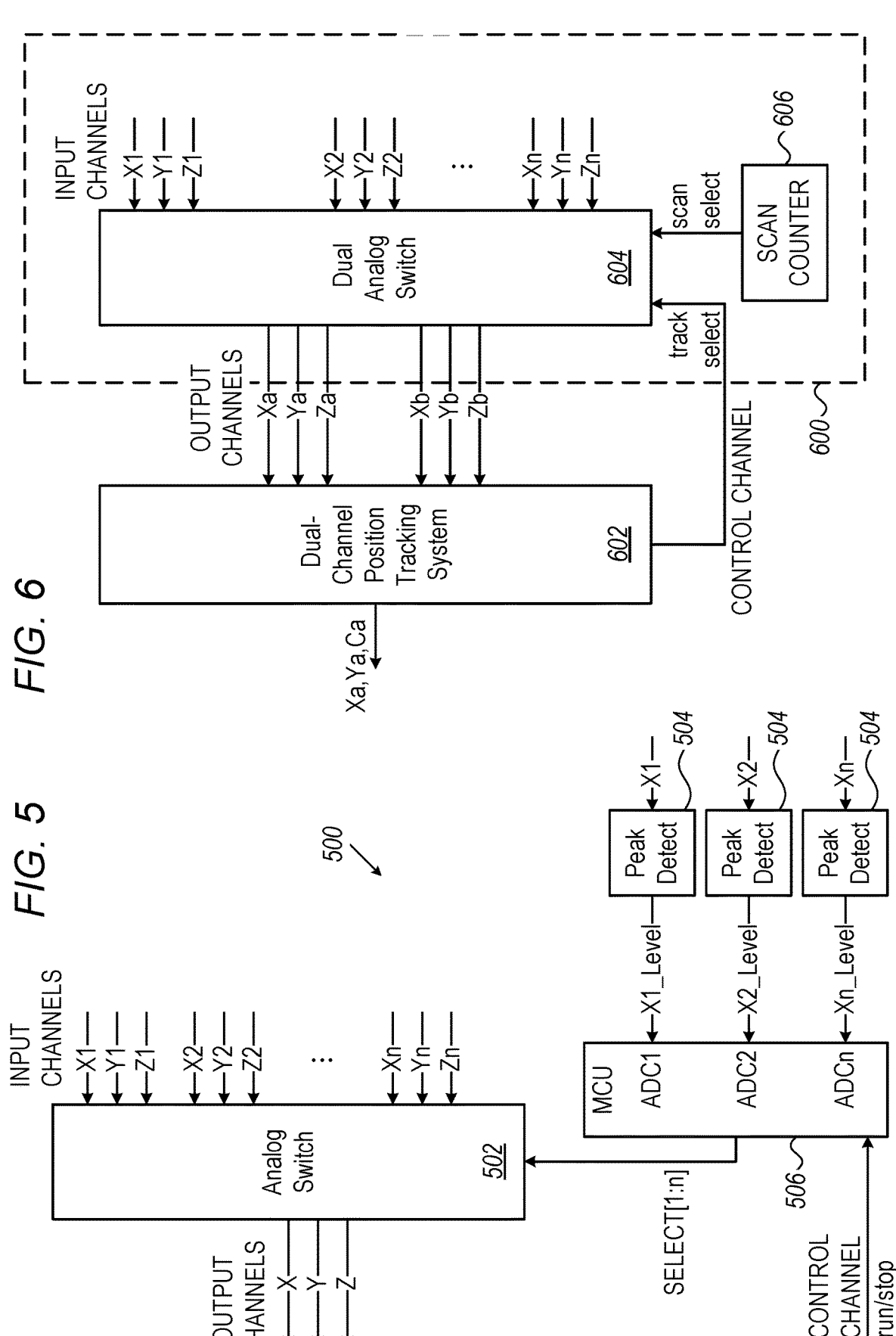
FIG. 5 is a block diagram that schematically illustrates the structure of a Time-Division-Multiplex detection with threshold-based preselection SPS, in accordance with an example of the present disclosure.
FIG. 6 is a block diagram that schematically illustrates the structure of an SPS and a Dual-Channel PTS, which are configured for concurrent track-and-detect, in accordance with an example of the present disclosure.

FIG. 5 is a block diagram that schematically illustrates the structure of a Time-Division-Multiplex detection with threshold-based preselection SPS 500, in accordance with an example of the present disclosure.

The SPS comprises an Analog Switch 502, peak-detectors 504 and a Microcontroller 506. The SPS receives X, Y and Z position indication signals from n instruments over the Input Channels, and outputs selected X, Y and Z position indication signals over the output channels.

Unlike SPS 400 (FIG. 4), which scans all input medical instruments and, thus, may be slow to detect that an instrument is in the working volume, SPS 500 preselects the medical instruments, and scans only those medical instruments for which the strength (e.g., voltage, or current) of the position indication signal is above a preset threshold, and, thus, in examples, SPS 500 will detect instruments in the working volume faster.

Referring, again, to FIG. 1, Magnetic Field Generators 36 confine an area around head 15 of patient 14; instruments outside that confined area are typically exposed to a magnetic field that is weaker than that to which instruments within the confined area are exposed.

Peak Detectors 504 are configured to latch peaks in the X position signals of the medical instruments. The latched peaks are input to analog-to-digital converters (ADCs) in a micro-controller-unit (MCU) 506.

If the Initial Phase is on (e.g., the PTS asserts the RUN input), the MCU will compare the digital representation of the peaks to a preset threshold, and send selection signals to Analog Switch 502, to scan all instruments for which the X-dimension position indication signal is above the threshold. SPS 500 will not scan medical instruments which do not meet the threshold criteria and, hence, cannot be in the working volume, shortening the detection time.

Concurrent Detection and Tracking

In some examples, the PTS concurrently tracks a medical instrument and checks if other medical instruments enter the working volume. If a new instrument is detected in the working volume, the PTS will track the new instrument.

FIG. 6 is a block diagram that schematically illustrates the structure of an SPS 600 and a Dual-Channel PTS 602, which are configured for concurrent Track-And-Detect, in accordance with an example of the present disclosure. Dual-Channel PTS 602 is configured to concurrently track a Tracked Instrument and to check if a Scanned Instrument is in the working volume.

SPS 600 comprises a Dual Analog Switch 604 and a Scan Counter 606. The Dual Analog Switch selects two sets of position indication signals from two medical instruments; the first set is selected according to a Scan-Select input, whereas the second set is selected according to the Track Select input. Scan Counter 606 continually counts, and the Scan Select serially points at all the input medical instruments. The Track Select input indicates the instrument to be tracked.

The Dual Channel PTS sends the Xa, Ya and Za position signals to Processor 202 (FIG. 2), for display. At the same time, Dual-Channel PTS 602 checks the position indication signals Xb, Yb, Zb of the scanned instruments. If the Dual-Channel PTS finds that the scanned instrument is in the working volume, the Dual-Channel PTS sets the Tracked Instrument to be the Detected Instrument, and changes the Track Select signals to point at the Detected Instrument. Thus, the tracked instrument will change to the newly detected instrument, and the scanning for yet newer instrument will continue.

The configurations of SPS 600 and a Dual-Channel PTS 602 illustrated in FIG. 6 and described above are cited by way of example. Other configurations may be used in alternative examples. In an example, a triple sample-and-hold circuit outputs the Xb, Yb and Zb signals; a single rather that a dual analog switch is used, and, whenever the scan counter points to the tracked instrument, the sample-and-hold circuit latches the Xa, Ya and Za signals. In another example, Dual-Channel Position Tracking System 602 sends the two SPS output channels to the processor and the processor calculates the locations and presents the tracked tool in the Display.

In yet other examples, a hybrid SPS may be used, employing both threshold-based instrument pre-selection (as described above, with reference to FIG. 5) and dual-channel tracking, as described above, with reference to FIG. 6.

Figures 7, 8:
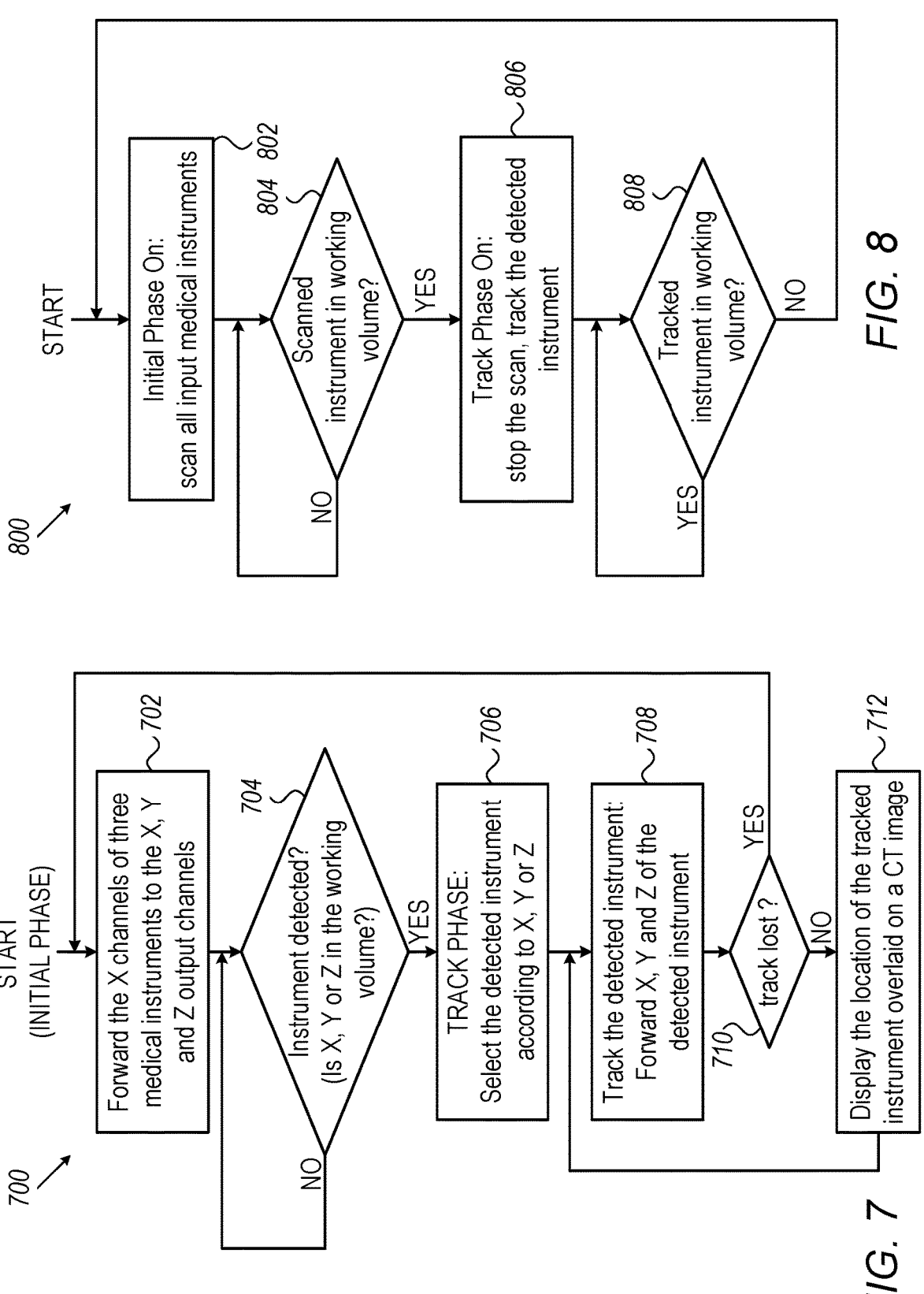
FIG. 7 is a flowchart that schematically illustrates a One-Dimension Detection method for the tracking of medical instruments, in accordance with an example of the present disclosure.
FIG. 8 is a flowchart that schematically illustrates a Time-Division-Multiplex detection method for the tracking of medical instruments, in accordance with an example of the present disclosure.

FIG. 7 is a flowchart 700 that schematically illustrates a One-Dimension Detection method for the tracking of medical instruments, in accordance with an example of the present disclosure. The flowchart is executed by Tracking and Display system 200 (FIG. 2).

The flowchart starts (typically upon power-up) at a Forward-X-Signals operation 702, wherein the SPS forwards the X position indication signals of the input medical instruments to the X, Y and Z outputs (and, thence, to the PTS). For example, if there are three medical instruments A, B and C, the SPS will forward the X-dimension position indication signal of instrument A to the X output position indication signal, the X-dimension signal of instrument B to the Y output, and the X-dimension signal of instrument C to the Z output. Thus, the PTS will receive the X, Y and Z position indication signals of a virtual combined-dimensions instrument that combines the three X-dimension signals of the three instruments.

Next, at a Detect Instrument operation 704, the PTS checks if the combined instrument is, in any of its three dimensions, in the working volume. In some examples, to determine whether an instrument is in the working volume, the PTS checks that the X position signal is between an X minimum and an X maximum value, the Y position signal is between a Y minimum and a Y maximum value, and, the Z position signal is between a Z minimum and a Z maximum value. Optionally, in some examples a processor (e.g., processor 206, FIG. 2) computes location of the sensors by triangulation of the transmitted magnetic fields from the sensors. However, when the tracking and display system is in the Initial Phase, the PTS checks if any of the X, Y and Z position indication signals is between the X minimum and the X maximum values.

As long as no position indication signal of any dimension is in the working volume, the tracking and display system remains in operation 704. When one of the X, Y or Z position indication signals is in the working volume, the tracking and display system enters the Track Phase, and, at a Select Detected Instrument operation 706, the PTS sends to the SPS a Select code according to the detected instrument. For example, if the Y position signal of the combined instrument is in the predefined X-dimension working volume, the PTS will send the code of instrument B, and the SPS, while in the Track Phase, will forward the X, Y and Z position indication signals of instrument B to the PTS.

At a Track-Detected-Instrument operation 708, the SPS continually sends the X, Y and Z position indication signals of the detected instrument to the PTS. At a Check-Lost-Track operation 710, the PTS checks if the tracked instrument is in the working volume—if it is not, the Tracking and Display system restarts the Initial Phase, and reenters Forward-X-Signals operation 702.

If, in operation 710, the tracked is still in the working volume, the tracking and display system enters a Display operation 712, wherein the location of the tracked instrument is overlaid on a CT-generated image of the organ that is displayed on Monitor 208 (FIG. 2). The Tracking and Display system then reenters operation 708, and remains in a loop, comprising operations 708-710-712 until the tracked instrument exits the working volume.

The configuration of flowchart 700 illustrated in FIG. 7 and described herein above is cited by way of example. Other configurations may be used in alternative examples. In some examples, more than three instruments may be used, and the PTS checks more than a single combined-dimension instrument. In another example, threshold preselection (as described with reference to FIG. 5) is used in conjunction with flowchart 700. In some examples, some of the instruments comprise less than three position indication signals, and in other examples some or all instruments may comprise, in addition, or instead of, some of the position indication signals, tilt and rotate indication signals.

FIG. 8 is a flowchart 800 that schematically illustrates a Time-Division-Multiplex detection method for the tracking of medical instruments, in accordance with an example of the present disclosure. The flowchart is executed by Tracking and Display system 200 (FIG. 2).

The flowchart starts at a Scan-All-Inputs operation 802; the Tracking and Display system is in the Initial Mode, and the PTS issues a Scan indication (over the control channel) and, responsively, the SPS sequentially forwards the position signals of all the instruments input over the Input Channel, to the Output Channel. In an example, the scanning is done by providing an increasing select code to an analog multiplexer, to sequentially forward the position signals of all inputs. After selecting the last instrument, the code resets to select the first instrument (and then keeps increasing).

Next, at a Check-Scanned-Instrument operation 804, the PTS checks if the scanned instrument is in the working volume (in the X, in the Y and in the Z dimensions). If the scanned instrument is not in the working volume, the tracking and display system reenters operation 802 to continue the scanning of input medical instruments.

If, in operation 804, the scanned instrument is in the working volume, the tracking and display system enters the Track Phase to track the detected instrument. The PTS stops the Scan indication and sends the position of the tracked instrument to processor 206 (FIG. 2), for display.

The tracked instrument may move during the Track Phase and may exit the working volume. At a Check-Tracked-Instrument operation 808, the PTS checks that the tracked instrument is still within the working volume and, if so, reenters operation 806. If, in operation 808, the tracked instrument is no longer in the working volume, the tracking and display system will reenter the Initial Phase, at operation 802.

The configuration of flowchart 800 illustrated in FIG. 8 and described herein above is cited by way of example. Other configurations may be used in alternative examples. In some examples, the scan does not include one or two instruments, which are always forwarded (e.g., reference coil 41, FIG. 1). In another example, threshold preselection (as described with reference to FIG. 5) is used in conjunction with flowchart 800. In some examples, some of the instruments comprise less than three position indication signals, and in other examples some or all instruments may comprise, in addition, or instead of, some of the position indication signals, tilt and rotate indication signals.

Although the examples described herein mainly address ENT applications, the methods and systems described herein can also be used in other applications, such as in cardiac, neurological, or ophthalmic applications.

The different elements of Tracking and Display System 200 (FIG. 2) may be implemented using suitable hardware, such as in one or more Application-Specific Integrated Circuits (ASICs) or Field-Programmable Gate Arrays (FP-GAS), using software, using hardware, or using a combination of hardware and software elements.

It will thus be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art.

EXAMPLES

Example 1

An apparatus includes a first plurality of input channels, a second plurality of output channels, a control channel, and switching circuitry. The input channels are configured to receive position signals from multiple medical instruments located in an organ of a patient. The output channels are configured to forward one or more of the position signals to a position tracking system. The control channel is configured to receive control signals from the position tracking system. The switching circuitry is configured to forward at least some of the position signals to at least some of the output channels in accordance with a first switching scheme, to receive from the position tracking system, over the control channel, in response to the position signals forwarded in accordance with the first switching scheme, a control signal indicative of a given medical instrument that was identified as being located within a working volume of the position tracking system, and to switch to a second switching scheme, in which all the position signals of the given medical instrument are forwarded to at least some of the output channels.

Example 2

The apparatus according to example 1, wherein, in accordance with the first switching scheme, the switching circuitry is configured to forward at least a single-axis position signal from each medical instrument.

Example 3

The apparatus according to example 1, wherein, in accordance with the first switching scheme, the switching circuitry is configured to alternate in time among the position signals of the multiple medical instruments.

Example 4

The apparatus according to example 3, further including a detector, which is configured to cause the switching circuitry to switch to the second switching scheme upon detecting that the given medical instrument is within the working area.

Example 5

The apparatus according to example 4, wherein the detector is configured to detect that the given medical instrument is within the working area by comparing magnitudes of at least some of the position signals to a threshold.

Example 6

The apparatus according to example 1, wherein the switching circuitry is configured to:

in accordance with the first switching scheme, (i) forward all the position signals of a certain medical instrument, different from the given medical instrument, to the output channels, and (ii) alternate in time among the position signals of the medical instruments other than the certain medical instrument; and in accordance with the second switching scheme, stop forwarding all the position signals of the certain medical instrument, and instead forward all the position signals of the given medical instrument.

Example 7

The apparatus according to example 1, wherein the output channels include three output channels arranged in a single output port, each of the output channels configured to output a respective single-axis position signal; and wherein the input channels include nine input channels arranged in three input ports, each of the input channels configured to receive a respective single-axis position signal.

Example 8

The apparatus according to example 1,
wherein the output channels include six output channels
arranged in two output ports, each of the output channels configured to output a respective single-axis posi-
tion signal; and
wherein the input channels are arranged in three or more
input ports, each of the input ports consisting of three
input channels, each of the input channels configured to
receive a respective single-axis position signal.

Example 9

The apparatus according to example 1, wherein the switching circuitry is further configured to:
after switching to the second switching scheme, receive
over the control channel a subsequent control signal
indicative of another medical instrument that was iden-
tified as being located within the working volume, and
to switch to a third switching scheme in which all the
position signals of the other medical instrument are
forwarded to at least some of the output channels.

Example 10

A method includes receiving, on a first plurality of input
channels, position signals from multiple medical instru-
ments located in an organ of a patient. One or more of the
position signals are forwarded to a position tracking system
on a second plurality of output channels. Control signals are
received on a control channel from the position tracking
system. At least some of the position signals are forwarded
to at least some of the output channels in accordance with a
first switching scheme. A control signal, indicative of a
given medical instrument that was identified as being
located within a working volume of the position tracking
system, is received from the position tracking system over
the control channel in response to the position signals
forwarded in accordance with the first switching scheme. A
switch is performed to a second switching scheme, in which
all the position signals of the given medical instrument are
forwarded to at least some of the output channels.

The invention claimed is:
1. An apparatus, comprising:
a first plurality of input channels configured to receive
position signals from multiple medical instruments
located in an organ of a patient;
a second plurality of output channels, configured to for-
ward one or more of the position signals to a position
tracking system;
a control channel configured to receive control signals
from the position tracking system; and
switching circuitry, configured to:
forward at least some of the position signals to at least
some of the output channels in accordance with a
first switching scheme;
receive from the position tracking system, over the
control channel, in response to the position signals
forwarded in accordance with the first switching
scheme, a control signal indicative of a given medi-
cal instrument that was identified as being located
within a working volume of the position tracking
system; and
switch to a second switching scheme, in which all the
position signals of the given medical instrument are
forwarded to at least some of the output channels, wherein, in accordance with the first switching
scheme, the switching circuitry is configured to
alternate in time among the position signals of the
multiple medical instruments.
2. The apparatus according to claim 1, wherein, in accor-
dance with the first switching scheme, the switching cir-
cuitry is configured to forward at least a single-axis position
signal from each medical instrument.
3. The apparatus according to claim 1, further comprising
a detector, which is configured to cause the switching
circuitry to switch to the second switching scheme upon
detecting that the given medical instrument is within the
working area.
4. The apparatus according to claim 3, wherein the
detector is configured to detect that the given medical
instrument is within the working area by comparing mag-
nitudes of at least some of the position signals to a threshold.
5. The apparatus according to claim 1, wherein the
switching circuitry is configured to:
in accordance with the first switching scheme, (i) forward
all the position signals of a certain medical instrument,
different from the given medical instrument, to the
output channels, and (ii) alternate in time among the
position signals of the medical instruments other than
the certain medical instrument; and
in accordance with the second switching scheme, stop
forwarding all the position signals of the certain medi-
cal instrument, and instead forward all the position
signals of the given medical instrument.
6. The apparatus according to claim 1,
wherein the output channels comprise three output chan-
nels arranged in a single output port, each of the output
channels configured to output a respective single-axis
position signal; and
wherein the input channels comprise nine input channels
arranged in three input ports, each of the input channels
configured to receive a respective single-axis position
signal.
7. The apparatus according to claim 1,
wherein the output channels comprise six output channels
arranged in two output ports, each of the output chan-
nels configured to output a respective single-axis posi-
tion signal; and
wherein the input channels are arranged in three or more
input ports, each of the input ports consisting of three
input channels, each of the input channels configured to
receive a respective single-axis position signal.
8. The apparatus according to claim 1, wherein the
switching circuitry is further configured to:
after switching to the second switching scheme, receive
over the control channel a subsequent control signal
indicative of another medical instrument that was iden-
tified as being located within the working volume, and
to switch to a third switching scheme in which all the
position signals of the other medical instrument are
forwarded to at least some of the output channels.
9. A method, comprising:
receiving, on a first plurality of input channels, position
signals from multiple medical instruments located in an
organ of a patient;
forwarding one or more of the position signals to a
position tracking system on a second plurality of output
channels;
receiving, on a control channel, control signals from the
position tracking system;
forwarding at least some of the position signals to at least
some of the output channels in accordance with a first switching scheme, wherein forwarding at least some of the position signals in accordance with the first switching scheme comprises alternating in time among the position signals of the multiple medical instruments;

receiving from the position tracking system, over the control channel, in response to the position signals forwarded in accordance with the first switching scheme, a control signal indicative of a given medical instrument that was identified as being located within a working volume of the position tracking system; and switching to a second switching scheme, in which all the position signals of the given medical instrument are forwarded to at least some of the output channels.

10. The method according to claim 9, wherein forwarding at least some of the position signals in accordance with the first switching scheme comprises forwarding at least a single-axis position signal from each medical instrument.

11. The method according to claim 9, wherein switching to the second switching scheme is performed upon detecting that the given medical instrument is within the working area.

12. The method according to claim 11, and comprising detecting that the given medical instrument is within the working area by comparing magnitudes of at least some of the position signals to a threshold.

13. The method according to claim 9, wherein:

forwarding at least some of the position signals in accordance with the first switching scheme comprises (i) forwarding all the position signals of a certain medical instrument, different from the given medical instrument, to the output channels, and (ii) alternating in time among the position signals of the medical instruments other than the certain medical instrument; and switching to the second switching scheme comprises, in accordance with the second switching scheme, stopping forwarding all the position signals of the certain medical instrument, and instead forwarding all the position signals of the given medical instrument.

14. The method according to claim 9, wherein the output channels comprise three output channels arranged in a single output port, each of the output channels configured to output a respective single-axis position signal; and wherein the input channels comprise nine input channels arranged in three input ports, each of the input channels configured to receive a respective single-axis position signal.

15. The method according to claim 9, wherein the output channels comprise six output channels arranged in two output ports, each of the output channels configured to output a respective single-axis position signal; and wherein the input channels are arranged in three or more input ports, each of the input ports consisting of three input channels, each of the input channels configured to receive a respective single-axis position signal.

16. The method according to claim 9, further comprising:

after switching to the second switching scheme, receiving over the control channel a subsequent control signal indicative of another medical instrument that was identified as being located within the working volume, and switching to a third switching scheme in which all the position signals of the other medical instrument are forwarded to at least some of the output channels.

* * * * *